United States Patent [19]

Fahmy et al.

[11] 4,263,318

[45] Apr. 21, 1981

[54] N-ALKOXY- AND N-ARYLOXYSULFINYLCARBAMATE ESTERS

[75] Inventors: Mohamed A. H. Fahmy; Tetsuo R. Fukuto, both of Riverside, Calif.

[73] Assignee: The Reagents of the University of California, Los Angeles, Calif.

[21] Appl. No.: 18,598

[22] Filed: Mar. 7, 1979

[51] Int. Cl.³ .................. A01N 43/16; C07D 317/44; C07D 307/82

[52] U.S. Cl. .............................. 424/282; 260/340.5 R; 260/340.9 R; 260/346.73; 260/347.2; 260/456 A; 424/285; 424/300; 549/33

[58] Field of Search ....... 260/346.73, 456 A, 340.5 R, 260/340.9 R; 424/285, 282

[56] References Cited

U.S. PATENT DOCUMENTS 4,148,910  4/1979  Hartmann et al. .............. 260/346.73

Primary Examiner—Ethel G. Love
Attorney, Agent, or Firm—Herzig & Walsh, Inc.

[57] ABSTRACT

A novel class of chemical compounds useful as pesticides consists of N-alkoxy- and N-aryloxysulfinylcarbamate esters. The preparation of these compounds and their formulation to control insects are exemplified.

40 Claims, No Drawings

N-ALKOXY- AND N-ARYLOXYSULFINYLCARBAMATE ESTERS

BACKGROUND OF THE INVENTION

This invention relates to the general field of pesticides, and is particularly concerned with the production of insecticides for the control of both household insects and crop insects.

U.S. Pat. No. 3,997,549 to Fukuto and Black discloses N-arylsulfenylated derivatives of benzofuranyl methylcarbamates as effective pesticides.

U.S. Pat. No. 4,006,231 to Black and Fukuto discloses N-aminosulfenylated derivatives of carbofuran as effective pesticides.

U.S. Pat. No. 3,843,689 to Brown discloses production of N-methyl or N-phenyldithiocarbamates produced from N-chlorothiocarbamates, as insecticides.

The object of the present invention is to provide another novel class of carbamate ester compounds which are effective pesticides, and procedure for preparing same.

SUMMARY OF THE INVENTION

The novel carbamate ester compounds of the invention are generally N-alkoxy- and N-aryloxysulfinylcarbamate esters. The compounds are prepared by reacting an N-chlorosulfinylcarbamate ester with an alcohol or a phenol, in a suitable organic solvent in the presence of a hydrogen chloride acceptor such as pyridine.

The resulting compounds of the invention are highly effective against certain pests and insects, and have substantially reduced mammalian toxicity, e.g. as compared to other potent insecticides such as carbofuran, described in U.S. Pat. No. 3,474,171. Thus, the invention compounds, while having high toxicity toward certain pests or insects, are relatively safe to mammals.

DETAILED DESCRIPTION OF THE INVENTION AND PREFERRED EMBODIMENTS

The sulfinylcarbamate esters or compounds of the invention have the formula noted below:

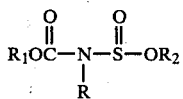  (1)

wherein R is a hydrocarbyl group containing from 1 to 12 carbon atoms; $R_1$ is selected from the class consisting of a hydrocarbyl group containing from 1 to 20 carbon atoms, a 5 to 6 membered heterocyclic ring containing O or S atoms, and the >C=N— group; and $R_2$ is selected from the class consisting of a hydrocarbyl group containing from 1 to 20 carbon atoms and a 5 to 6 membered heterocyclic ring.

Thus, R is a hydrocarbyl (hydrocarbon) group containing only hydrogen and carbon, either aliphatic or aromatic; preferably a straight chain, branched or carbocyclic (five or six membered ring) alkyl, phenylalkyl or phenyl, and containing from 1 to 12 carbon atoms, and further exemplified hereinafter.

$R_1$ can be a hydrocarbyl group containing only hydrogen and carbon, and from 1 to 20 carbon atoms, either aliphatic or aromatic, including substituted or unsubstituted alkyl, cycloalkyl, phenylalkyl and naphthylalkyl; and substituted or unsubstituted aryl, such as phenyl and naphthyl; and wherein the aforementioned groups can be substituted with one or more halogen, cyano, nitro, alkyl, alkylthio and alkoxy groups, a 5 or 6 membered heterocyclic ring containing O or S atoms, e.g. benzothienyl, furanyl, benzofuranyl and 1,3-benzodioxolyl; or the >C=N— group; The >C=N— group can be represented more specifically by the formula:

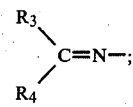

where
$R_3$ is hydrogen, alkyl, alkylthio or cyano, and
$R_4$ is alkyl, alkylthio, alkoxy, alkanoyl, alkoxycarbonyl, dialkylaminocarbonyl or phenyl, all of which can be unsubstituted or substituted with one or more cyano, nitro, alkylthio, alkylsulfinyl, alkylsulfonyl or alkoxy groups.

Where $R_1$ is aryl, preferred examples of such aryl groups are as follows:

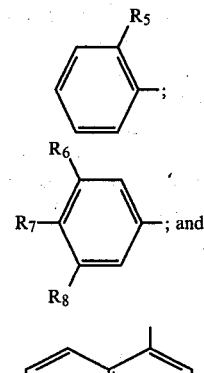

where
$R_5$ is hydrogen, alkylthio, alkyl, alkylthioalkyl, 2-dioxalanyl or halogen, e.g. Cl or Br;
$R_6$ is alkyl, alkoxy, alkoxyalkyl or halogen;
$R_7$ is hydrogen, alkyl, halogen, alkylthio alkoxy, dialkylamino or formyl (alkyl) amino;
$R_8$ is hydrogen or alkyl;
and wherein the number of aliphatic carbon atoms in $R_3$, $R_4$, $R_5$, $R_6$, $R_7$, and $R_8$, individually should not exceed eight:

$R_2$ can be a hydrocarbyl group, either aliphatic or aromatic, e.g. unsubstituted or substituted alkyl, including unsaturated alkyl, such as allyl and propargyl, cycloalkyl, phenylalkyl naphthylalkyl; or a five to six membered heterocyclic ring, which includes in any combination, O or S atoms, e.g. one or two oxygen or sulfur atoms, e.g. furanyl; and wherein the permissible substituents on said groups are one or more halogen, cyano nitro, dialkylamino, alkyl, alkylthio or alkoxy groups; or $R_2$ can be aryl, e.g. phenyl or naphthyl, unsubstituted or substituted in any position by one or more alkyl, cycloalkyl, alkylthio, alkoxy, or halogen groups; and $R_2$ contains 1 to 20 carbon atoms.

Preferred carbamates of the invention are those of formula (1) above, where R is a hydrocarbyl group containing from 1 to 12 carbon atoms; $R_1$ is selected from the class consisting of hydrocarbyl groups containing from 1 to 12 carbon atoms, hererocyclic rings containing O or S atoms, and containing 5 to 6 members in the heterocyclic nucleus, and a group containing the >C=N— radical; and $R_2$ is a hydrocarbyl group containing from 1 to 12 carbon atoms.

Thus, in one group of preferred carbamate ester compounds of the invention, $R_1$ is a hydrocarbyl group containing from 1 to 12 carbon atoms, either aliphatic or aromatic, including alkyl, e.g. methyl, ethyl, isopropyl, propyl, isobutyl, cycloalkyl, e.g. cyclohexyl, phenylalkyl, naphthylalkyl; aryl, e.g. phenyl, naphthyl, alkylphenyl, e.g. tolyl, xylyl, alkylnaphthyl, any of which can contain substituents such as halogen, e.g. chlorine or bromine, alkoxy, alkylthio and dialkylamino, and R is alkyl, phenyl, phenylalkyl and naphthylalkyl groups, as exemplified above, containing 1–12 carbon atoms. Particularly preferred are those compounds where $R_1$ is alkyl, phenyl, alkylphenyl and naphthyl groups, and which can be unsubstituted or substituted e.g. with halogen, alkoxy, dialkylamino, alkylthio groups, and the like, and especially wherein $R_1$ is 3-alkylphenyl such as 3-isopropyl- and 3-sec-butylphenyl, 2-alkoxyphenyl such as 2-isopropoxyphenyl or 1-naphthyl. Particularly preferred also is the group of carbamate esters wherein $R_1$ is a heterocyclic ring, and including fused-on heterocyclic rings, containing one or two O or S atoms, and 5 to 6 members in the heterocyclic nucleus, e.g. benzofuranyl or 1,3-benzodioxolyl, and especially a 2,3-dihydrobenzofuranyl-7 group having the formula (2) below, and the 1,3-benzodioxol-4 group having the formula (3) below:

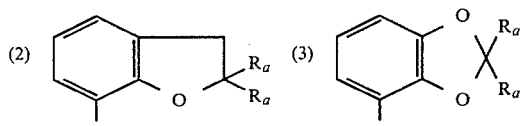

where $R_a$ is an alkyl group of 1 to about 4 carbon atoms, e.g. methyl, ethyl, propyl, n-butyl, and both $R_a$'s can be the same or different, and most preferably wherein $R_1$ is the 2,3-dihydro-2,2-dimethylbenzofuranyl-7group or the 2,2-dimethyl-1,3-benzodioxal-4 group; and R is alkyl. Another particularly preferred class of carbamates of the invention are those wherein $R_1$ is a group containing the >C=N— radical, as defined above, and R is alkyl. Such >C=N— groups can be, for example, the following:

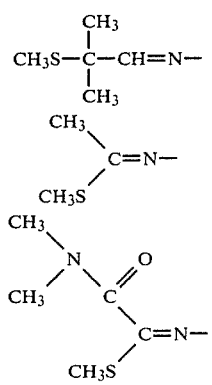

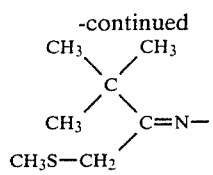

$R_2$ in all of the above preferred components is a hydrocarbyl group containing from 1 to 12 carbon atoms, preferably alkyl or aryl, and more preferably, alkyl, phenyl or alkylphenyl. Among the preferred alkyl groups are methyl, ethyl, isopropyl, tert.-butyl, n-butyl, with an increasing number of carbon atoms up to dodecyl. Such alkyl groups can be substituted with halogen, e.g. chlorine or bromine, nitro, alkoxy, alkylthio, dialkylamino, cyano or phenyl. Examples of such substituents are 2,2,2-trichloroethyl, methoxy- or ethoxyethyl, 2-nitroethyl, 2-methylthioethyl, diethylaminoethyl, benzyl, halobenzyl, e.g. 4-chlorobenzyl and 2,2,2-trichloro-1-(4-chlorophenyl)ethyl, and the like. Among the preferred aryl groups are substituted phenyl, preferred substituents being alkyl, alkoxy and halogen. The preferred position of such substituents on the phenyl nucleus is the 2-position, such as 2-tolyl, 2,6-xylyl, 2-ethyl and 2-isopropyl, separately or in combination with other substituents in other positions.

The N-alkoxy- and N-aryloxysulfinylcarbamate esters of the invention can be prepared by the following general reaction scheme:

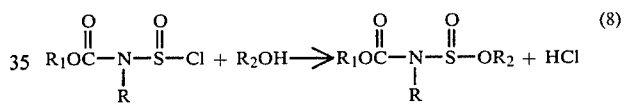

werein R, $R_1$, and $R_2$ are as defined above. The N-chlorosulfinylcarbamate ester intermediate is formed by the reaction of the corresponding carbamate with thionyl chloride, preferably using pyridine as hydrogen chloride acceptor in an inactive polar solvent such as tetrahydrofuran. Non-polar solvents such as hexane also may be used. Such ester can be formed in high yield using essentially equivalent quantities of the carbamate and thionyl chloride and slightly more than an equivalent amount of pyridine. These novel intermediates are described in the copending application Ser. No. 18,416 filed Mar. 7, 1979 by M. A. H. Fahmy and T. R. Fukuto.

Without isolation, the N-chlorosulfinylcarbamate ester intermediates can react in situ with alcohols and phenols, in the presence of an equivalent amount of pyridine as hydrogen chloride acceptor to form N-alkoxy- and N-aryloxysulfinylcarbamate esters. The temperature of the reaction medium varies according to the reactivity of the alcohol or the phenol. In general, the reaction can be carried out at temperatures from 10° to 60° C.

It will be understood that if desired, the N-chlorosulfinylcarbamate ester starting material in reaction (8) above can be initially prepared and isolated as an intermediate compound, and such compound then reacted with the appropriate $R_2OH$ compound as noted in the above reaction scheme.

The following examples are representative of the novel compounds of this invention.

EXAMPLE I

Synthesis of
2,3-dihydro-2,2-dimethylbenzofuranyl-7(methyl)(hexoxysulfinyl)carbamate A mixture of 2,3-dihydro-2,2-dimethylbenzofuranyl-7-methyl-carbamate (5.5 g, 0.025 mol), pyridine (2.5 g, 0.032 mol), thionyl chloride (3.0 g, 0.025 mol), and 25 ml anhydrous tetrahydrofuran, was stirred at room temperature for 6 hours. Pyridine hydrochloride separates immediately after mixing, and continued stirring is to insure complete reaction. To this mixture was added 2 g of pyridine (0.025 mol) followed by 3 g hexyl alcohol (0.029 mol) added dropwise. After stirred for an additional hour, 150 ether were added to the reaction mixture. The mixture was washed with water three (30 ml each) times. The ether solution was dried over anhydrous sodium sulfate, filtered and concentrated under vacuum. Unreacted carbamate (about 0.5 g) crystallized out and was filtered. The remaining liquid, 7.5 g was almost free from unreacted carbamate as evident from the NMR spectrum of this crude product.

A sample of this product was further purified by preparative thin layer chromatography using ether-hexane (3:1) mixture as the developing solvent.

Analysis calculated for $C_{18}H_{27}O_5NS$; Carbon, 58.51%, Hydrogen, 7.37%. Found: Carbon, 59.24%, Hydrogen, 8.08%.

EXAMPLE II

Synthesis of
2,3-dihydro-2,2-dimethylbenzofuranyl-7(methyl)(t-butoxysulfinyl)carbamate A mixture of 2,3-dihydro-2,2-dimethylbenzofuranyl-7 methylcarbamate (4.4 g, 0.02 mol), pyridine (1.9 g, 0.024 mol), thionyl chloride (2.5 g, 0.021 mol), tetrahydrofuran (20 ml, anhydrous), was stirred at room temperature for 6 hours. To this mixture was added 2 pyridine (0.025 mol) followed by 2.0 g t-butanol (0.027 mol) added dropwise. After stirring for an additional hour, the reaction mixture was worked up similar to Example 1. The oily residue after solvent evaporation and subjection to high vacuum was found to be a pure single compound as shown by NMR spectrum.

Analysis calculated for $C_{16}H_{23}O_5NS$; Carbon, 56.28%, Hydrogen, 6.79%. Found: Carbon, 56.74%, Hydrogen, 6.32%.

EXAMPLE III

Synthesis of
2,3-dihydro-2,2-dimethylbenzofuranyl-7(methyl)(n-butoxysulfinyl)carbamate A mixture of 2,3-dihydro-2,2-dimethylbenzofuranyl-7methyl-carbamate (4.4 g, 0.02 mol), pyridine (2 g, 0.025 mol), thionyl chloride (2.7 g, 0.023 mol), tetrahydrofuran (20 ml, annhydrous), was stirred at room temperature for 6 hours. To this mixture was added 2 g pyridine (0.025 mol) followed by 2.5 n-butanol (0.034 mol) added dropwise. After stirring for an additional hour, the reaction mixture was worked up similar to previous examples. The oily residue after solvent evaporation was subjected to high vacuum. A sample was further purified by preparative thin layer chromatography, which gave an essentially pure product.

Analysis calculated for $C_{16}H_{23}O_5NS$; Carbon, 56.28%, Hydrogen, 6.79%. Found: Carbon, 56.21%, Hydrogen, 6.94%.

EXAMPLE IV

Synthesis of
2,3-dihydro-2,2-dimethylbenzofuranyl-7(methyl)(phenoxysulfinyl)carbamate A mixture of 2,3-dihydro-2,2-dimethylbenzofuranyl-7methylcarbamate (4.4 g, 0.02 mol), pyridine (2 g, 0.025 mol), thionyl chloride (2.5 g, 0.021 mol), tetrahydrofuran (20 ml, anhydrous), was stirred at room temperature for 6 hours. To this mixture was added 2 g pyridine (0.025 mol) followed by 2.0 g phenol (0.021 mol) in 5 ml tetrahydrofuran added dropwise. After stirring for an additional hour, the reaction mixture was worked up in the usual manner as described in previous examples. The product was an oil. A sample was further purified by thin layer chromatography as described above for other analogs.

Analysis calculated for $C_{18}H_{19}O_5NS$, Carbon, 59.82%, Hydrogen, 5.3%. Found: Carbon, 61.19%, Hydrogen 5.38%.

EXAMPLE V

Synthesis of
2,3-dihydro-2,2-dimethylbenzofuranyl-7(methyl)(2,6-dimethylphenoxysulfinyl)carbamate A mixture of 2,3-dihydro-2,2-dimethylbenzofuranyl-7methylcarbamate (4.4 g, 0.02 mol), pyridine (2 g, 0.025 mol), thionyl chloride (2.5 g, 0.021 mol), and 20 ml tetrahydrofuran, was stirred at room temperature for 12 hours. To this mixture was added 2 g pyridine (0.025 mol) followed by 2.5 g (0.021 mol) 2,6-dimethylphenol in 5 ml tetrahydrofuran added dropwise.

Work up following the general procedure of Example I, resulted in 7.1 g of product, 91% yield.

Analysis calculated for $C_{20}H_{23}O_5NS$; Carbon, 61.68%, Hydrogen, 5.95%. Found: Carbon, 62.02%, Hydrogen 6.29%.

EXAMPLE VI

Synthesis of 3-isopropylphenyl
(methyl)(n-butoxysulfinyl)carbamate

To a solution of 3-isopropylphenyl methylcarbamate (3.5 g, 0.018 mol) in 20 ml anhydrous tetrahydrofuran was added 1.9 g pyridine (0.024 mol) and 2.5 g thionyl chloride (0.021 mol). The mixture was stirred for 12 hours at room temperature in order to insure complete conversion of the carbamate to the N-chlorosulfinyl derivative. Pyridine (2 g, 0.025 mol) was added and followed by 2 g n-butanol (0.027 mol) added dropwise. The mixture was stirred for an additional hour at room temperature and worked up similarly to previous examples. A sample was purified by thin layer chromatography as previously described.

Analysis calculated for $C_{15}H_{23}O_4NS$; Carbon, 57.48%, Hydrogen, 7.40%. Found: Carbon, 57.80%, Hydrogen, 7.21%.

EXAMPLE VII

Synthesis of 3-isopropylphenyl
(methyl)(n-hexoxysulfinyl)carbamate

To a solution of 3-isopropylphenyl methylcarbamate (3.8 g, 0.02 mol) in 20 ml anhydrous tetrahydrofuran was added 2.0 g pyridine (0.025 mol) and 2.5 g thionyl chloride (0.021 mol). The mixture was stirred for 12 hours at room temperature. Pyridine (2 g, 0.025 mol) was added and followed by 2.5 g of 1-hexanol (0.025 mol) added dropwise. Workup and purification according to procedure described for other derivatives yielded 6.5 g of the desired product (95% yield).

Analysis calculated for $C_{17}H_{27}O_4NS$, Carbon, 59.8%, Hydrogen, 7.97%. Found: Carbon, 60.43%, Hydrogen, 8.52%.

EXAMPLE VIII

Synthesis of 2-isopropoxyphenyl (methyl)(n-hexoxysulfinyl)carbamate

To a solution of 2-isopropoxyphenyl methylcarbamate (4.2 g, 0.02 mol), in 20 ml anhydrous tetrahydrofuran was added 2.0 g pyridine (0.025 mol) and 2.5 g thionyl chloride (0.021 mol). The mixture was stirred for 12 hours at room temperature. Pyridine (2 g, 0.025 mol) was added and followed by 2.5 g of 1-hexanol (0.025 mol) added dropwise.

Workup and purification according to procedures described for earlier examples resulted in 6.7 g of product (94% yield).

Analysis calculated for $C_{17}H_{27}O_5NS$, Carbon, 57.13%, Hydrogen, 7.62%. Found: Carbon, 57.43%, Hydrogen, 7.99%.

EXAMPLE IX

Synthesis of 2-isopropoxyphenyl (methyl)(t-butoxysulfinyl)carbamate

To a solution of 2-isopropoxyphenyl methylcarbamate (4.2 g, 0.02 mol), in 20 ml anhydrous tetrahydrofuran, was added 2.0 g pyridine (0.025 mol) and 2.5 g thionyl chloride (0.021 mol). The mixture was stirred for 12 hours at room temperature. Pyridine (2.0 g, 0.025 mol) was added and 2.0 g of t-butanol (0.027 mol) was added to the mixture dropwise.

Workup according to procedure described in the previous examples resulted in 6.6 g of pure product (92% yield).

Analysis calculated for $C_{15}H_{23}O_5NS$, Carbon, 54.69%, Hydrogen, 7.04%. Found: Carbon, 55.16%, Hydrogen, 7.00%.

EXAMPLE X

Synthesis of S-methyl N-[N'-methyl-N'-hexoxysulfinylcarbamoyloxy]thioacetimidate To a solution of S-methyl N-(N'-methylcarbamoyloxy)thioacetimidate (3.3 g, 0.02 mol) in 20 ml anhydrous tetrahydrofuran, was added 2.5 g thionyl chloride (0.021 mol) and 2.0 g pyridine (0.025 mol). The mixture was stirred for 4 hours at a temperature between 15°-18° C. Two grams of pyridine (0.025 mol) were added followed by 2.5 g of 1-hexanol (0.025 mol) added dropwise at the same temperature.

Workup as described for other examples resulted in an oily residue. A sample of this residue was further purified by preparative thin layer chromatography using ether-hexane as the developing solvent. The pure product obtained was a waxy solid.

Analysis calculated for $C_{11}H_{22}O_4N_2S_2$, Carbon, 42.58%, Hydrogen, 7.15%. Found: Carbon, 43.62%, Hydrogen, 7.67%.

EXAMPLE XI p Synthesis of S-methyl N-[N'-methyl-N'-butoxysulfinylcarbamoyloxy]thioacetimidate To a solution of S-methyl N-(N'-methylcarbamoyloxy)thioacetimidate (3.3 g, 0.02 mol) in 20 ml anhydrous tetrahydrofuran was added 2.5 g thionyl chloride (0.021 mol) and 2.0 g pyridine (0.025 mol). The mixture was stirred at room temperature for 4 hours and 2.0 g pyridine (0.025 mol) were added. Then, 1-butanol (1.6 g, 0.02 mol) was added dropwise at the same time temperature. The mixture was stirred for an additional hour at room temperature and worked up as described for previous examples. The oily product was crystallized from benzene-hexane to give 3.5 g of product m.p. 52°-54° C.

Analysis calculated for $C_9H_{18}O_4N_2S_2$, Carbon, 38.28%, Hydrogen, 6.42%. Found: Carbon, 38.71%, Hydrogen, 6.57%.

EXAMPLE XII

Snythesis of 2-methyl-2-(methylthio)propionaldehyde O-[(methyl)(decoxysulfinyl)carbamoyl]oxime To a solution of 2-methyl-2-(methylthio)propionaldehyde O-(methylcarbamoyl)oxime (3.8 g, 0.02 mol) in 20 ml anhydrous tetrahydrofuran was added 2.0 g pyridine (0.025 mol) and 2.5 g thionyl chloride (0.021 mol). The mixture was stirred for 6 hours at 18°-20° C. Pyridine (2.0 g, 0.025 mol) was added and followed by 3.5 g 1-decanol (0.022 mol) added dropwise. The mixture was worked up in a manner similar to other examples and the resulting oily residue was filtered from unchanged carbamate.

Purification by preparative thin layer chromatography resulted in a pure product.

Analysis calculated for $C_{17}H_{34}N_2O_4S_2$, Carbon, 51.74%, Hydrogen, 8.69%. Found: Carbon, 51.99%, Hydrogen, 8.55%.

EXAMPLE XIII

Synthesis of 1-naphthyl(methyl)(hexoxysulfinyl)carbamate

To a solution of 1-naphthyl methylcarbamate (4.0 g, 0.02 mol) in 20 ml of anhydrous tetrahydrofuran was added 2.0 g pyridine (0.025 mol), and 2.5 g thionyl chloride (0.021 mol). The mixture was stirred for 12 hours at room temperature. Pyridine (2.0 g, 0.025 mol) was added followed by 2.5 g 1-hexanol (0.025 mol) added dropwise at the same temperature.

Workup in the usual manner resulted in an oily residue. Purification using preparative thin layer chromatography yielded a pure product.

Analysis calculated for $C_{18}H_{23}O_4NS$, Carbon, 61.87%, Hydrogen, 6.63%. Found: Carbon, 61.94%, Hydrogen, 6.65%.

EXAMPLE XIV

Synthesis of isopropyl (phenyl)(N-butoxysulfinyl)carbamate

Isopropyl (phenyl)(chlorosulfinyl)carbamate (5.2 g, 0.02 mol), prepared from thionyl chloride and isopropyl phenylcarbamate as described in the above Ser. No. 18,416, was dissolved in 30 ml anhydrous methylene chloride. To this solution was added 2.0 g pyridine followed by 1.6 g n-butanol (0.02 mol), added dropwise with stirring. Stirring was continued for an additional 1 hour at room temperature. The mixture was worked up according to procedures described for other examples and the oily residue was distilled. Product boiling at 110–112/0.04 mm was collected.

Analysis calculated for $C_{14}H_{21}O_4NS$, Carbon, 56.16%, Hydrogen, 7.07%. Found: Carbon, 57.09%, Hydrogen 7.14%.

The following are additional examples of the sulfinyl carbamate compounds of the invention:

2,3-Dihydro-2,2-dimethylbenzofuranyl-7 [2,2,2-trichloro-1-(4-Chlorophenyl)-ethoxysulfinyl](methyl)-carbamate 2,3-Dihydro-2,2-dimethylbenzofuranyl-7 (2,2,2-trichloroethoxy-sulfinyl) (methyl)carbamate 2,3-Dihydro-2,2-dimethylbenzofuranyl-7 (ethoxysulfinyl)(methyl)carbamate 2,2-Dimethyl-1,3-benzodioxolyl-4 (n-butoxysulfinyl)-(methyl)carbamate S-Methyl N',N'-dimethyl-N-(n-butoxysulfinyl)(methyl)carbamoyloxy-1-thiooximidate 1-Naphthyl (3,4-methylenedioxybenzyl)(methyl)carbamate S-Methyl N-[(2-methoxyethoxysulfinyl)(methyl)carbamoyloxy]thioacetimidate 2,3-Dihydro-2,2-dimethylbenzofuranyl-7 (2-methoxyethoxysulfinyl)(methyl)carbamate 2,3-Dihydro-2,2-dimethylbenzofuranyl-7 (2-nitroethoxysulfinyl)(methyl)carbamate Isopropyl (4-chlorobenzyloxysulfinyl)(phenyl)carbamate n-Butyl (ethoxysulfinyl)(ethyl)carbamate 2-Chlorophenyl (octoxysulfinyl)(methyl)carbamate 2-Methyl-2-(methylthio)propionaldehyde O-[(hexoysulfinyl)(methyl)carbamoyl]oxime S-Methyl N-[(2,2,2-trichloroethoxysulfinyl)(methyl)-carbamoyloxy]thioacetimidate 2,3-Dihydro-2,2-dimethylbenzofuranyl-7 (methyl)(proparagyloxysulfinyl)carbamate The insecticidal N-alkoxy- and N-aryloxysulfinylcarbamate esters of the invention may be formulated with the usual carriers, including additives and extenders used in the preparation of insecticidal compositions. Thus, the toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material.

The present compounds may be made into liquid concentrates by solution or emulsification in suitable liquid such as organic solvents, and into solid cocentrates by admixing with talc, clays, and other known solid carriers used in the insecticide art. These concentrates are compositions containing about 5–50% toxicant and the rest inert material which includes dispersing agents, emulsifying agents, and wetting agents. The concentrates are diluted for practical application, with water or other liquid for liquid sprays or with additional solid carrier for application as a dust or granular formuation.

The concentration of the toxicant in the dilution generally used for application is normally in the range of about 2% to about 0.001%. Many variations of spraying and dusting compositions in the art may be used, by substituting a compound of this invention into compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of the carbamate ester compounds of the invention should be employed.

BIOLOGICAL ACTIVITY

Representative compounds of the N-aryloxy- and N-alkoxysulfinylcarbamate esters of the invention were tested for insecticidal activity against two insect species, house flies, Musca domestica, and mosquito larvae, Culex pipiens. Stock 1% concentrated solutions of each of the test compounds were made in acetone, and such solutions diluted with acetone to a concentration of 0.001–0.1%. House files were treated topically on the notum by 1 $\mu L$ of each of the diluted acetone solutions and percent mortality was counted 24 hours after application. Insects were held at a constant temperature of 60° F. Larvicidal activity was determined by applying 1 ml of the acetone solutions in 100 ml of water containing 20 3rd instar mosquito larvae. Results are presented as $LD_{50}$ in $\mu g/g$ for house flies and $LC_{50}$ in ppm for mosquito larvae.

Mammalian toxicity was determined against Swiss white mice. The test compound was applied orally using corn oil as the carrier. Results are given as $LD_{50}$ in mg of compound per kg body weight. The toxicological data for a number of typical N-aryloxy- and N-alkoxysulfinylcarbamates of the invention are summarized in Table I.

The term "$LD_{50}$" represents the dose needed to kill 50% of the test animals, and the term "$LC_{50}$" is the concentration needed to kill 50% of the mosquito larvae. In interpreting the values in the table below, the lower the value for $LD_{50}$ for house flies and for $LC_{50}$ for mosquito larvae, the greater the insecticidal potency or toxicity of that particular compound. On the other hand, the higher the value of $LD_{50}$ for mice, the lower the mammaliam toxicity or the greater is the mammalian safety of such compound.

TABLE I

Toxicity of N-aryloxy- and N-alkoxysulfinylcarbamates of Examples I to XIII against house flies, mosquito larvae and white mice

| Compound of Example | House flies $LD_{50}$ ($\mu g/g$) | Culex $LC_{50}$ (ppm) | Mice $LD_{50}$ (mg/kg) |
|---|---|---|---|
| III | 16 | | 160 |
| II | 2.2 | 0.0058 | 40 |
| I | 13 | 0.0025 | 280 |
| IV | 6.4 | 0.0055 | 42 |
| V | 13.5 | | ˋ100 |
| VI | 50 | | |
| VII | 80 | | >1000 |
| VIII | 42 | 0.01 | >1000 |
| IX | 65 | | 400 |
| XI | 5.5 | | |
| X | 6.5 | | 260 |
| XII | 11.5 | 0.006 | 60 |
| XIII | 360 | | >1000 |

The relatively low values for the various compounds of the invention listed in Table I for $LD_{50}$ for house flies and $LC_{50}$ for mosquito larvae (Culex) indicates high toxicity of the invention compounds as against such insects. Thus, for example the parent material of the compounds of Examples I to V of Table I, carbofuran, which is 2,3-dihydro-2,2-dimethyl-7-benzofuranyl methylcarbamate, has an $LD_{50}$ value for house flies, of about 6.5. The $LD_{50}$ values for house flies of the related invention compounds of Examples I through V, are comparable, ranging from 2.2 to 16, thus showing comparable insecticidal toxicity of such invention compounds to the potent insecticide carbofuran. However, and of particular significance, the mammalian toxicity of the invention compounds of Examples I to V of Table I above, as indicated by their high $LD_{50}$ values ranging from 40 to 280 for mice, is low, as compared to the much higher toxicity as indicated by an $LD_{50}$ value of from about 2 to about 8, found for the parent carbamate ester insecticide, carbofuran. Also compound XII is of comparable toxicity to house flies as the parent carbamate aldicarb, which is 2-methyl-2-(methylthio)-propionaldehyde 0-(methylcarbamoyl)oxime. However, XII is much safer to mammals ($LD_{50}=60$ mg/kg) as compared to aldicarb ($LD_{50}=0.3-0.5$ mg/kg). Thus, the above Table shows that the N-alkoxy-and N-aryloxysulfinylcarbamate esters of the invention have high insecticidal activity or potency, but have substantially reduced mammalian toxicity or substantially greater mammalian safety.

While we have described particular embodiments of the invention for purposes of illustration, it will be understood that various changes and modifications within the spirit of the invention can be made, and the invention is not to be taken as limited except by the scope of the appended claims.

What is claimed is:

1. Carbamates having pesticidal activity of the formula:

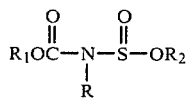

wherein R is a hydrocarbyl group containing from 1 to 12 carbon atoms; $R_1$ is selected from the class consisting of a hydrocarbyl group containing from 1 to 20 carbon atoms, a 5 to 6 membered heterocyclic ring consisting essentially of one to two O or S atoms, the remaining ring atoms being carbon atoms, and the >C=N-group; and $R_2$ is selected from the class consisting of a hydrocarbyl group containing from 1 to 20 carbon atoms and a 5 to 6 membered heterocyclic ring consisting essentially of one to two O or S atoms, the remaining ring atoms being carbon atoms.

2. Carbamates as defined in claim 1, wherein $R_1$ is the group

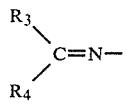

where
$R_3$ is hydrogen, alkyl, alkylthio or cyano, and
$R_4$ is alkyl, alkylthio, alkoxy, alkanoyl, alkoxycarbonyl, dialkylaminocarbonyl, or phenyl, which can be unsubstituted or substituted with cyano, nitro, alkylthio, alkylsulfinyl, alkylsulfonyl or alkoxy groups, the number of aliphatic carbon atoms in $R_3$ and $R_4$ not exceeding eight.

3. Carbamates as defined in claim 1, wherein $R_1$ is an aryl group selected from the class consisting of:

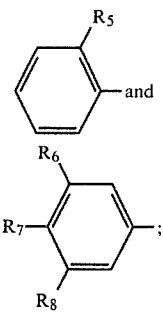

where
$R_5$ is hydrogen, alkoxy, alkylthio, alkyl, alkylthioalkyl, 2-dioxalanyl, or halogen;
$R_6$ is alkyl, alkoxy, alkoxyalkyl, or halogen;
$R_7$ is hydrogen, alkyl, halogen, alkylthio, alkoxy, dialkylamino or formyl(alkyl)amino; and
$R_8$ is hydrogen or alkyl;
the number of aliphatic carbon atoms in $R_5$, $R_6$, $R_7$, and $R_8$, individually, not exceeding eight.

4. Carbamates as defined in claim 3, wherein $R_1$ is:

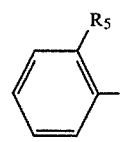

5. Carbamates as defined in claim 3, wherein $R_1$ is:

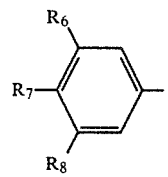

6. Carbamates as defined in claim 1, wherein $R_1$ is 1-naphthyl.

7. Carbamates as defined in claim 1, where $R_1$ is a 5 to 6 membered heterocyclic ring consisting essentially of one to two O or S atoms, the remaining ring atoms being carbon atoms.

8. Carbamates as defined in claim 1, wherein $R_2$ is substituted or unsubstituted alkyl, cycloalkyl, phenylalkyl, naphthylalkyl, or a five to six membered heterocyclic ring which consists essentially of one to two O or S atoms, the remaining ring atoms being carbon atoms, and wherein said groups can be substituted by one or more halogen, cyano, nitro, dialkylamino, alkyl, alkylthio, or alkoxy groups; phenyl or naphthyl, unsubstituted or substituted by one or more alkyl, cycloalkyl, alkylthio, alkoxy, or halogen groups.

9. Carbamates as defined in claim 1, wherein R and $R_2$ are each alkyl.

10. Carbamates as defined in claim 1, wherein R is alkyl and $R_2$ is aryl.

11. Carbamates having pesticidal activity of the formula:

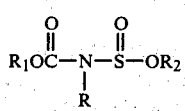

where R is a hydrocarbyl group containing from 1 to 12 carbon atoms; $R_1$ is selected from the class consisting of hydrocarbyl groups containing from 1 to 12 carbon atoms, heterocyclic rings consisting essentially of one to two O or S atoms, the remaining atoms being carbon atoms, and containing 5 to 6 members in the heterocyclic nucleus, and groups containing the >C=N- radical; and $R_2$ is a hydrocarbyl group containing from 1 to 12 carbon atoms.

12. Carbamates as defined in claim 11, wherein R is selected from the group consisting of alkyl, phenyl, phenylalkyl and naphthylalkyl.

13. Carbamates as defined in claim 11, wherein $R_2$ is selected from the group consisting of alkyl, phenyl and alkylphenyl.

14. Carbamates as defined in claim 11, wherein $R_1$ is a hydrocarbyl group containing from 1 to 12 carbon atoms, and $R_2$ is selected from the group consisting of alkyl, phenyl, and alkylphenyl.

15. Carbamates as defined in claim 14, wherein $R_1$ is selected from the group consisting of alkyl, phenyl, alkylphenyl and naphthyl, and R is selected from the group consisting of alkyl, phenyl, phenylalkyl and naphthylalkyl.

16. Carbamates as defined in claim 11, wherein $R_1$ is selected from the group consisting of 3-isopropylphenyl, 3-sec-butylphenyl, 2-isopropoxyphenyl and 1-naphthyl.

17. Carbamates as defined in claim 11, wherein $R_1$ is a heterocyclic ring consisting essentially of one to two O or S atoms the remaining atoms being carbon atoms, and containing 5 to 6 members in the hetero-cyclic nucleus.

18. Carbamates as defined in claim 17, wherein R is alkyl, and $R_2$ is selected from the group consisting of alkyl, phenyl, and alkylphenyl.

19. Carbamates as defined in claim 17, wherein $R_1$ is a benzofuranyl or a 1,3-benzodioxolyl group.

20. Carbamates as defined in claim 19, wherein R is alkyl and $R_2$ is selected from the group consisting of alkyl, phenyl, and alkylphenyl.

21. Carbamates as defined in claim 11, wherein $R_1$ is selected from the class having the formulae:

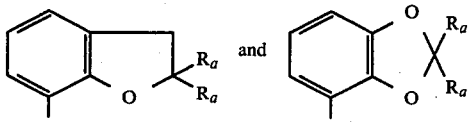

where $R_a$ is an alkyl group of 1 to about 4 carbon atoms, and both $R_a$'s can be the same or different, R is alkyl, and $R_2$ is selected from the group consisting of alkyl, phenyl and alkylphenyl.

22. Carbamates as defined in claim 11, wherein $R_1$ is the 2,3-dihydro-2,2-dimethylbenzofuranyl-7 group, or the 2,2-dimethyl-1,3--benzodioxol-4 group, R is alkyl and $R_2$ is selected from the group consisting of alkyl, phenyl, and alkylphenyl.

23. Carbamates as defined in claim 22, wherein R is methyl.

24. Carbamates as defined in claim 11, wherein $R_1$ is selected from the class having the formulae:

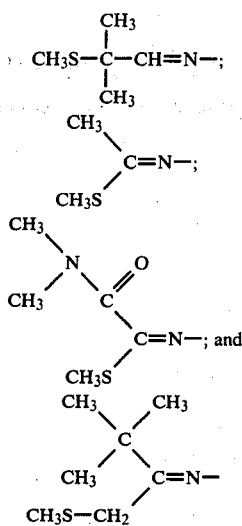

25. Carbamates as defined in claim 24, wherein R is alkyl and $R_2$ is selected from the group consisting of alkyl, phenyl, and alkylphenyl.

26. Carbamates as defined in claim 25, wherein R is methyl.

27. Carbamates as defined in claim 25, wherein $R_1$ is the group having the formula:

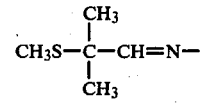

and R is methyl.

28. 2,3-dihydro-2,2-dimethylbenzofuranyl-7-(methyl)(hexoxysulfinyl)carbamate.

29. Carbamate as defined in claim 1, which is 3-isopropylphenyl (methyl)(n-butoxysulfinyl)carbamate.

30. Carbamate as defined in claim 1, which is 2-methyl-2-(methylthio)propionaldehyde 0-[(methyl)(decoxysulfinyl)carbamoyl]oxime.

31. Carbamate as defined in claim 1, which is 2-isopropoxyphenyl (methyl)(n-hexoxysulfinyl)carbamate.

32. Carbamate as defined in claim 1, which is S-Methyl N',N'-dimethyl-N-(n-butoxysulfinyl)(methyl)-carbamoyloxy-1-thio-oximidate.

33. An insecticidal composition comprising an insecticidally effective amount of a carbamate as defined in claim 1, in admixture with a carrier.

34. An insecticidal composition comprising an insecticidally effective amount of a carbamate as defined in claim 11, in admixture with a carrier.

35. An insecticidal composition comprising an insecticidally effective amount of a carbamate as defined in claim 21, in admixture with a carrier.

36. An insecticidal composition comprising an insecticidally effective amount of a carbamate as defined in claim 25, in admixture with a carrier.

37. The method of controlling insects which comprises applying to the sites of infestation an insecticidally effective amount of a compound as defined in claim 1.

38. The method of controlling insects which comprises applying to the sites of infestation an insecticidally effective amount of a compound as defined in claim 11.

39. The method of controlling insects which comprises applying to the sites of infestation an insecticidally effective amount of a compound as defined in claim 23.

40. The method of controlling insects which comprises applying to the sites of infestation an insecticidally effective amount of a compound as defined in claim 26.

* * * * *